US005482710A

United States Patent [19]
Slavtcheff et al.

[11] Patent Number: 5,482,710
[45] Date of Patent: Jan. 9, 1996

[54] COSMETIC COMPOSITION FOR TREATMENT OF PIMPLES AND REDNESS

[75] Inventors: Craig S. Slavtcheff, Cheshire; Stephen R. Barrow, Trumbull; Vispi D. Kanga, Shelton; Michael C. Cheney, Fairfield; Alexander Znaiden, Trumbull, all of Conn.

[73] Assignee: Chesebrough-Pond'USA Co., Division of Conopco, Inc., Greenwich, Conn.

[21] Appl. No.: 99,876

[22] Filed: Jul. 30, 1993

[51] Int. Cl.$^6$ .............................. A61K 7/32; A61K 7/36; A61K 7/38; A61K 7/42

[52] U.S. Cl. .................... 424/195.1; 424/DIG. 5; 424/DIG. 65; 424/DIG. 67; 424/ DIG. 68; 514/783; 514/844; 514/845; 514/846; 514/847; 514/859

[58] Field of Search ........................ 514/844, 859, 514/783; 424/195, 195.1

[56] References Cited

U.S. PATENT DOCUMENTS

| | | | |
|---|---|---|---|
| 3,920,835 | 11/1975 | Van Scott et al. | 514/460 |
| 3,984,470 | 10/1976 | Binon et al. | 564/229 |
| 3,988,470 | 10/1976 | Van Scott et al. | 514/451 |
| 4,021,572 | 5/1977 | Van Scott et al. | 514/557 |
| 4,105,782 | 8/1978 | Yu et al | 514/613 |
| 4,105,783 | 8/1978 | Yu et al. | 514/459 |
| 4,536,399 | 8/1985 | Flynn et al. | 514/63 |
| 4,540,567 | 9/1985 | Oneto et al. | 424/45 |
| 4,545,990 | 10/1985 | Le Foyer de Costil et al. | 514/557 |
| 4,608,370 | 8/1986 | Aronsohn | 514/159 |
| 4,613,592 | 9/1986 | Benzoni | 514/63 |
| 4,772,592 | 9/1986 | Benzoni | 514/63 |
| 4,880,621 | 11/1989 | Grollier et al. | 424/74 |
| 4,933,177 | 6/1990 | Grollier et al. | 424/74 |
| 4,961,927 | 10/1990 | Kogure | 424/94.3 |
| 5,057,502 | 10/1991 | Walsh | 514/54 |
| 5,091,171 | 2/1992 | Yu et al. | 424/642 |

FOREIGN PATENT DOCUMENTS

| | | | |
|---|---|---|---|
| 0508324 | 10/1992 | European Pat. Off. | 514/847 |
| 04359999 | 12/1992 | Japan | 252/106 |
| 04356424 | 12/1992 | Japan | 514/844 |
| 2130486 | 6/1984 | United Kingdom | 514/859 |

OTHER PUBLICATIONS

International Search Report, Dec. 12, 1994.
H. Fey & I. Otte "Worterbuch Der Kosmetik"–p. 29, 1985.

*Primary Examiner*—Dale R. Ore
*Attorney, Agent, or Firm*—Milton L. Honig

[57] ABSTRACT

A cosmetic composition is provided which includes at least one keratolytic agent and a combination of water-soluble and water-insoluble anti-irritancy agents in a pharmaceutically acceptable carrier. Most effective is a combination of a $C_7$–$C_{30}$ β-hydroxy carboxylic acids such as salicylic acid with a $C_1$–$C_{25}$ α-hydroxy carboxylic acid such as glycolic or lactic acids. The water-soluble anti-irritancy agent is preferably a salt of glycyrrhizinic acid. The water-insoluble anti-irritancy agent is preferably α-bisabolol, azulene or combinations thereof. Other performance components may include a $C_1$–$C_{10}$ alkyl lactate and an antimicrobial agent such as a zinc or aluminum salt.

9 Claims, No Drawings

COSMETIC COMPOSITION FOR TREATMENT OF PIMPLES AND REDNESS

BACKGROUND OF THE INVENTION

1. Field of the Invention

The invention concerns a cosmetic composition that when applied to the skin, especially the face, is effective against pimples and redness.

2. The Related Art

Pimples and reddened skin areas are of great concern to both juveniles and adults. These skin problems can arise either from disease conditions or as a result of skin changes associated with aging or hormonal changes. Disease conditions include those of dry skin, ichthyosis, eczema, palmar and plantar hyperkeratoses, dandruff, acne and warts. Skin changes associated with aging may include such symptoms as age spots, wrinkling and related aging changes.

U.S. Pat. Nos. 4,105,782, 4,105,783, 4,021,572, 3,879,537, 3,920,835, 3,984,470 and 3,988,470, all to Van Scott and Yu, report on the use of α-hydroxyacids for the treatment of diseased skin. These patents especially focus upon lower molecular weight α-hydroxyacids such as lactic and glycolic acids. Ammonium salts were found to be more effective than the free acid, and both of the aforementioned forms were said to be substantially better than the alkali metal salts. A problem with this technology is that when the α-hydroxyacids are present at levels sufficient to be effective, they cause a stinging sensation and even redness on the skin. Indeed, the art considers the stinging and redness as a sign of effective performance. Consumers, of course, would prefer performance without side effects.

More recently, U.S. Pat. No. 5,091,171 (Yu et al) disclosed the use of α-hydroxyacids for treatment of non-disease conditions.

A rich source of literature is available that describes treatment of acne vulgaris. For instance, U.S. Pat. No. 4,536,399 (Flynn et al) reports the combination of benzoyl peroxide or salicylic acid with fumed silica intended to treat oily skin. Benzoyl peroxide based anti-acne compositions with irritation suppressants are described in U.S. Pat. No. 4,545,990 (Le Foyer de Costil et al). U.S. Pat. No. 4,608,370 (Aronsohn) reports removal of at least some blemishes and the imparting of a useful, healthy complexion with a composition of salicylic acid, resorcinol, lactic acid and ethyl alcohol. Other ache treatments are reported in U.S. Pat. Nos. 4,613,592 and 4,772,592, both to Benzoni. These treatments utilize $C_1$–$C_4$ alkyl lactates as the active ingredient in a water-in-oil emulsion.

A slightly different approach is found in U.S. Pat. No. 5,057,502 (Walsh) which utilizes Juniper extract materials to thin heavy oily, greasy secretions from the skin. Co-actives are reported to be vitamin A, aloe vera and camomile extract. Pulverized flowers are reported in the skin treatments of U.S. Pat. Nos. 4,880,621, 4,933,177, both to Grollier et al. Even though the many aforementioned treatments may be effective, consumers are not satisfied with either the speed of performance or results from these formulations.

Accordingly, it is an object of the present invention to provide a cosmetic composition that can eliminate pimples, blemishes and redness within a short period after application.

It is another object of the present invention to provide a cosmetic composition for the treatment of pimples, blemishes and redness which avoids any undesirable side effects such as stinging and heightened skin color.

These and other objects of the present invention will become more readily apparent from consideration of the following summary, detailed description and examples which follow.

SUMMARY OF THE INVENTION

A cosmetic composition is provided that includes:
(i) from about 0.1 to about 10% of at least one keratolytic agent each selected from the group consisting of $C_7$–$C_{30}$ β-hydroxy carboxylic acids and their salts, $C_1$–$C_{25}$ α-hydroxy carboxylic acids and their salts and mixtures thereof.
(ii) from about 0.0001 to about 5% by weight each of an anti-irritancy agent combination which includes:
  (a) a water-soluble anti-irritancy material which is a $C_{20}$–$C_{100}$ saponin; and
  (b) a water-insoluble anti-irritancy agent selected from the group consisting of $C_7$–$C_{30}$ polycyclic polyenes, $C_{15}$–$C_{40}$ triterpenes and mixtures thereof, the water-soluble and water-insoluble anti-irritancy agents being present in a relative weight ratio from about 20:1 to 1:20; and
(iii) from about 1 to about 99.9% by weight of a pharmaceutically acceptable carrier.

Particularly suitable as the α-hydroxy carboxylic acids are glycolic, lactic and 2-hydroxyoctanoic acids as well as their alkali metal and ammonium salts. The preferred β-hydroxy carboxylic acid is salicylic acid and its alkali metal and ammonium salts. Especially useful is a combination of α- and β-hydroxy carboxylic acids. Glycyrrhizinic acid and salts thereof, especially the dipotassium and ammonium salts, are the preferred water-soluble anti-irritancy agents α-Bisabolol and azulene are the preferred water-insoluble anti-irritancy agents.

DETAILED DESCRIPTION

Now there has been found a cosmetic composition formulated with at least one keratolytic agent which is either α-hydroxy or β-hydroxy carboxylic acid and a combination of two types of anti-irritancy agent. This composition rapidly reduces the size of blemishes and reduces overall redness. Stinging sensations often associated with hydroxy carboxylic acids are no longer a problem with the combination of actives.

Accordingly, a first critical component of compositions according to the present invention is that of a keratolytic agent. Under the class of keratolytic agents there are two categories useful for the present invention.

The first category is represented by $C_7$–$C_{30}$ β-hydroxy carboxylic acids and their salts. Illustrative of this category is salicylic acid as well as the alkalimetal and ammonium salts thereof. Suitable amounts of salicylic acid or salt forms may range from about 0.1 to about 10%, preferably between about 0.8 and about 2.5%, optimally between about 1 and 1.5% by weight.

The second category of keratolytic agent is represented by $C_1$–$C_{25}$ α-hydroxy carboxylic acids of Formula I, having the structure:

wherein R and $R^1$ are H, F, Cl, Br, alkyl, aralkyl or aryl groups of saturated or unsaturated, isomeric or nonisomeric, straight or branched chain, having 1 to 25 carbon atoms, or cyclic form having 5 or 6 ring members, and in addition, R and $R^1$ may carry OH, CHO, COOH and alkoxy groups having 1 to 9 carbon atoms, the α-hydroxyacid existing as a free acid or lactone form, or in salt form with an organic amine base or an inorganic alkali, and as stereoisomers, and D, L, and DL forms when R and $R^1$ are not identical.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2-hydroxynonanoic acid; 2-hydroxydecanoic acid; 2-hydroxyundecanoic acid; 2-hydroxydodecanoic acid (α-hydroxylauric acid); 2-hydroxytetradecanoic acid (α-hydroxymyristic acid); 2-hydroxyhexadecanoic acid (α-hydroxypalmitic acid); 2-hydroxyoctadecanoic acid (α-hydroxystearic acid); 2-hydroxyeicosanoic acid (α-hydroxyarachidontc acid); 2-phenyl 2-hydroxyethanoic acid (mandelic acid); 2,2-diphenyl 2-hydroxyethanoic acid (benzilic acid); 3-phenyl 2-hydroxypropanoic acid (phenyllactic acid); 2-phenyl 2-methyl 2-hydroxyethanoic acid (atrolactic acid); 2-(4'-hydroxyphenyl) 2-hydroxyethanoic acid; 2-(4'-chlorophenyl 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3-(2-hydroxyphenyl) 2-hydroxypropanoic acid; 3-(4'-hydroxyphenyl) 2-hydroxypropanoic acid; and 2-(3',4'-dihydroxyphenyl) 2-hydroxyethanoic acid.

Most preferred of this group of materials are glycolic acid, lactic acid and 2-hydroxyoctanoic acid and salts thereof. The salts may be selected from alkalimetal, ammonium and $C_1$–$C_{20}$ alkyl or alkanol ammonium counterions. Levels of α-hydroxyalkanoic acids may range from about 0.1 to about 10%, preferably between about 0.2 and 1%, optimally between about 0.4 and 0.5% by weight.

In a particularly preferred embodiment, there will be present a mixture of both a β-hydroxy carboxylic acid and an α-hydroxy carboxylic acid. For instance, the optimum combination is a mixture of salicylic acid and glycolic acid in a relative weight ratio from about 20:1 to about 1:20, preferably from about 10:1 to 1:1, optimally from about 3:1 to about 2:1.

Compositions of the present invention can include a variety of anti-irritancy agents. These are either water-soluble or water-insoluble (i.e. oil-soluble). The water-soluble anti-irritancy agents should be $C_{20}$–$C_{100}$ saponins, primary examples of which are glycyrrhizinic acid, especially the alkalimetal and ammonium salts. The water-insoluble anti-irritancy agents should be selected from $C_7$–$C_{30}$ polycyclic polyenes, $C_{15}$–$C_{40}$ triterpenes and mixtures thereof. Representative of the polyenes is azulene (synthetically derived or extracted from yarrow). Representative of the triterpenes is α-bisabolol (synthetically derived or extracted from chamomile). Each of these can be present at levels ranging from about 0.0001 to about 5%, preferably from about 0.001 to about 1%, optimally from about 0.01 to about 0.5% by weight. Most especially preferred is dipotassium glycyrrhizinate. Amounts of this material may range from about 0.001 to about 3%, preferably from about 0.1 to about 0.5%, optimally between about 0.15 and 0.2% by weight.

In a preferred embodiment, the cosmetic composition of the present invention will include a combination of dipotassium glycyrrhizinate and α-bisabolol. These will be present in a weight ratio of about 20:1 to 1:20, preferably between about 5:1 and 1:5, optimally between about 3:1 and about 1:3 by weight.

A still further component of compositions according to the present invention may be $C_1$–$C_{10}$ alkyl lactates. Most preferred is ethyl lactate which may be present in amounts ranging from about 0.01 to about 5%, preferably between about 0.5 and 3%, optimally between about 1.5 and 2.5% by weight.

A variety of herbal extracts may be included as components of the composition. These extracts may include those of thyme, rosemary, myrrh, bitter orange, coltsfoot and sage. Each of these may range in an amount anywhere from about 0.00001 to about 2%, preferably between about 0.01 and about 0.5% by weight.

Compositions of the invention preferably also contain aloe extract to assist with skin adhesion. Aloe extract levels may range from about 0.01 to about 5%, preferably from about 0.05 to 1%, optimally between 0.1 and 0.75% by weight.

Antimicrobial agents may also be useful in compositions of the present invention. Typically the antimicrobial agent may be material such as triclosan tricarbanilide, tea tree oil, farnesol, farnesol acetate, hexachlorophene, $C_4$–$C_{20}$ quaternary ammonium salts such as benzolconium chloride and a variety of zinc or aluminum salts. Typically the zinc or aluminum salts are compounds such as zinc pyridinethione, zinc sulphate, zinc chloride, zinc phenolsulphonate, aluminum chloride, aluminum sulphate and aluminum chlorhydrate. Amounts of the antimicrobial agent may range from about 0.1 to about 5%, preferably from about 0.2 to about 1%, optimally about 0.3% by weight.

Compositions of the present invention may either be aqueous or anhydrous. Preferably the compositions are aqueous. Water will then be present in amounts which may range from about 5 to about 90%, preferably from about 30 to about 55%, optimally between about 35 and 45% by weight.

Besides water, relatively volatile solvents may also be incorporated within compositions of the present invention. Most preferred are monohydric $C_1$–$C_3$ alkanols. These include ethyl alcohol, methyl alcohol and isopropyl alcohol. The amount of monohydric alkanol may range from about 5 to about 50%, preferably from about 15 to about 40%, optimally between about 25 to 35% by weight.

Emollient materials in the form of silicone oils and synthetic esters may be incorporated into compositions of the present invention. Amounts of the emollients may range anywhere from about 0.1 to about 30%, preferably between about 1 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Among the ester emollients are:

(1) Alkenyl esters of fatty acids having 10 to 20 carbon atoms. Examples thereof include oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and all-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Most preferred from the foregoing list of esters are PEG-40 hydrogenated castor oil (available as Cremophore RH40®) and PPG-10-cetyl ether (available as Procetyl-10®).

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners/viscosifiers in amounts up to about 5% by weight of the composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those said by B. F. Goodrich under the Carbopol trademark.

Collectively the water, solvents, silicones, esters, humectants and/or thickeners are viewed as pharmaceutically acceptable carriers for the keratolytic and anti-irritancy agents. Total amount of carrier will range from about 1 to 99.9%, preferably from about 80 to 99% by weight.

Cosmetic compositions of the present invention may be in any form. These forms may include lotions, creams, sticks, roll-on formulations, mousses, aerosol sprays, pad-applied formulations, and overnight facial masks.

A particularly preferred embodiment of the present invention is that the actives be incorporated into a quick-drying gel or paste that forms a peelable facial mask. A film-forming and an adhesion promoting polymer are necessary in this product form. Polyvinyl alcohol can serve as the film-forming polymer. Preferably the polyvinyl alcohol will be present as a low and high molecular weight species. The former will have a number average molecular weight ranging from about 15,000 to 27,000. The higher polyvinyl alcohol material will have a number average molecular weight ranging from about 44,000 to 65,000. These materials are available from the Air Products Company under the trademark, Airvol 205S® and Airvol 523®. Amounts of total polyvinyl alcohol will range from about 2 to about 40%, preferably from about 10 to about 20%, optimally between about 10 and 15% by weight. The ratio of low to high molecular weight may range from about 1:20 to 20:1, preferably from about 1:10 to 1:1, optimally from about 1:5 to 1:3, respectively.

As the adhesion promoting polymer, it is preferable to employ a hydrophobic acrylate or methacrylate polymer. Especially useful is Pemulen TR2® from the B. F. Goodrich Company. The CTFA name is acrylates/$C_{10}$–$C_{30}$ alkyl acrylate cross-polymer. The adhesion-promoting polymer will be present in amounts from about 0.1 to about 20%, preferably from about 0.5 to about 5%, more preferably from about 1 to about 2% by weight.

The following examples will more fully illustrate select embodiments of this invention. All parts, percentages and proportions referred to herein and in the appended claims are by weight unless otherwise indicated.

EXAMPLE 1

Illustrative formulas for a water-rinseable, skin cleanser and toner are listed below.

| INGREDIENT | Formula (Weight %) | | | | |
|---|---|---|---|---|---|
| | 1 | 2 | 3 | 4 | 5 |
| Carbopol 934 ® (2% aqueous solution) | 30.0 | 30.0 | 30.0 | 30.0 | 30.0 |
| Polyalphaolefin (3.8 cst) | 18.0 | 18.0 | 18.0 | 18.0 | 18.0 |
| Glycerin | 4.0 | 4.0 | 4.0 | 4.0 | 4.0 |
| Stearyl alcohol | 3.0 | 3.0 | 3.0 | 3.0 | 3.0 |
| Borax | 2.5 | 2.5 | 2.5 | 2.5 | 2.5 |
| Ceteareth-20 | 2.0 | 2.0 | 2.0 | 2.0 | 2.0 |
| Benzyl alcohol | 1.5 | 1.5 | 1.5 | 1.5 | 1.5 |
| Salicylic acid | 1.5 | 1.5 | 1.5 | 1.0 | 1.0 |
| Glycolic acid | 1.0 | 1.0 | 1.0 | 1.5 | 1.5 |
| Diammonium glycyrrhizinate | 0.5 | 0.5 | 0.5 | 0.5 | 0.5 |
| α-Bisabolol | 0.1 | — | 0.1 | 0.4 | — |
| Azulene | — | 0.1 | 0.1 | — | 0.4 |
| Methylparaben | 0.2 | 0.2 | 0.2 | 0.2 | 0.2 |
| Propylparaben | 0.1 | 0.1 | 0.1 | 0.1 | 0.1 |
| Disodium EDTA | 0.1 | 0.1 | 0.1 | 0.1 | 0.1 |
| Water | Balance | Balance | Balance | Balance | Balance |

EXAMPLE 2

Illustrative cream formulas according to the present invention are described below.

| INGREDIENT | Formula (Weight %) | | | | |
|---|---|---|---|---|---|
| | 6 | 7 | 8 | 9 | 10 |
| Silicone Oil Q2-3225C | 32.0 | 32.0 | 32.0 | 20.0 | 15.0 |
| Ethanol | 10.0 | 10.0 | 10.0 | 10.0 | 10.0 |

-continued

| INGREDIENT | Formula (Weight %) | | | | |
|---|---|---|---|---|---|
| | 6 | 7 | 8 | 9 | 10 |
| Isopropanol | 12.0 | 5.0 | 5.0 | 5.0 | 5.0 |
| Diisopropyl myristate | 5.0 | 8.5 | 8.5 | 8.5 | 8.5 |
| Sorbitan trioleate | 2.5 | 2.5 | 2.5 | 2.5 | 2.5 |
| Zinc phenolsulfonate | 0.5 | 0.5 | 0.5 | 0.5 | 0.5 |
| Salicylic acid | 1.0 | 0.8 | 0.5 | 0.5 | 0.5 |
| Ammonium lactate | 0.5 | 0.5 | — | — | — |
| Ammonium glycolate | — | — | 0.5 | 0.5 | 0.5 |
| t-Butyl lactate | 0.3 | 0.3 | — | — | — |
| Ethyl lactate | — | — | 0.3 | 0.3 | 0.3 |
| Disodium glycyrrhizinate | 0.5 | 0.5 | 0.5 | 0.5 | 0.3 |
| α-Bisabolol | 0.3 | 0.3 | 0.3 | 0.3 | 0.5 |
| DMDM Hydantoin | 0.2 | 0.2 | 0.2 | 0.2 | 0.2 |
| Fragrance | 0.1 | 0.1 | 0.1 | 0.1 | 0.1 |
| Water | Balance | Balance | Balance | Balance | Balance |

EXAMPLE 3

Illustrative anhydrous stick formulas according to the present invention are described below.

| INGREDIENT | Formula (Weight %) | | |
|---|---|---|---|
| | 11 | 12 | 13 |
| Cyclomethicone | 40.3 | 40.7 | 40.7 |
| Stearyl alcohol | 30.0 | 30.0 | 30.0 |
| Hydrogenated castor oil | 20.0 | 20.0 | 20.0 |
| Talc | 5.0 | 5.0 | 5.0 |
| PEG-8-Distearate | 2.0 | 2.0 | 2.0 |
| Salicylic acid | 1.5 | 1.5 | 1.5 |
| Glycolic acid | 0.8 | 0.4 | 0.4 |
| Dipotassium glycyrrhizinate | 0.3 | 0.3 | 0.2 |
| α-Bisabolol | 0.1 | 0.1 | 0.2 |

EXAMPLE 4

Illustrative aqueous stick formulas according to the present invention are described below.

| INGREDIENT | Formula (Weight %) | | |
|---|---|---|---|
| | 14 | 15 | 16 |
| Water | 39.7 | 40.3 | 40.8 |
| Propylene glycol | 40.0 | 40.0 | 40.0 |
| Sodium stearate | 10.0 | 10.0 | 10.0 |
| Poloxamer 1307 ® | 8.0 | 8.0 | 8.0 |
| Sodium Salicylate | 2.0 | 1.5 | 1.0 |
| Dipotassium glycyrrhizinate | 0.2 | 0.2 | 0.2 |
| α-Bisabolol | 0.1 | — | — |

EXAMPLE 5

Illustrative anhydrous ointment formulas according to the present invention are described below.

| INGREDIENT | Formula (Weight %) | | |
|---|---|---|---|
| | 17 | 18 | 19 |
| Zinc Oxide | 38.1 | 38.3 | 38.2 |

-continued

| INGREDIENT | Formula (Weight %) | | |
|---|---|---|---|
| | 17 | 18 | 19 |
| Cod liver oil | 25.0 | 25.0 | 25.0 |
| Lanolin | 15.0 | 15.0 | 15.0 |
| Petrolatum | 10.0 | 10.0 | 10.0 |
| Talc | 9.5 | 9.5 | 9.5 |
| Salicylic acid | 2.0 | 2.0 | 1.0 |
| Glycolic acid | — | — | 1.0 |
| Dipotassium glycyrrhizinate | 0.2 | 0.2 | 0.2 |
| α-Bisabolol | 0.1 | — | — |
| Azulene | 0.1 | — | 0.1 |

EXAMPLE 6

A series of illustrative overnight facial masks according to the present invention and their clinical performance are described below. Each formula is a combination of an aqueous (A), alcoholic (B) and oily (C) phase.

| INGREDIENT* | FORMULA (Weight %) | | | | | |
|---|---|---|---|---|---|---|
| | 20 | 21 | 22 | 23 | 24 | 25 |
| Phase A | | | | | | |
| Water | 43.000 | 42.000 | 39.000 | 39.000 | 40.500 | 40.500 |
| Zinc sulfate | 0.300 | 0.300 | 0.300 | 0.300 | 0.300 | 0.300 |
| Polyvinyl alcohol (PVA-205) | 2.500 | 2.800 | 2.800 | 2.800 | 2.800 | 2.800 |
| Polyvinyl alcohol (PVA-523) | 9.000 | 9.500 | 9.500 | 9.500 | 10.000 | 10.000 |
| Polyethylene glycol-20000 | 0.050 | 0.100 | 0.100 | 0.100 | 0.100 | 0.100 |
| Aloe extract, 40x | 0.750 | 0.750 | 0.750 | 0.750 | 0.750 | 0.750 |
| Propylene glycol | 4.000 | 4.000 | 4.000 | 4.000 | 4.000 | 4.000 |
| Propylene glycol-4 | 1.500 | 1.000 | 1.000 | 1.000 | 1.000 | 1.000 |
| Dipotassium glycyrrizinate | — | 0.100 | 0.250 | 0.250 | 0.150 | 0.150 |
| Phase B | | | | | | |
| Alcohol SD-40 | 28.850 | 29.450 | 32.300 | 33.100 | 30.020 | 27.770 |
| Salicylic acid | 1.300 | 1.300 | 1.300 | 0.500 | 0.750 | 1.500 |
| Glycolic acid | 0.200 | 0.200 | 0.200 | 0.200 | 0.400 | 0.400 |
| Ethyl lactate | 1.000 | 1.000 | 1.000 | 1.000 | 1.500 | 3.000 |
| Myrrh HS | 0.500 | 0.500 | 0.500 | 0,500 | 0.500 | 0.500 |
| Rosemary HS | 0.500 | 0.500 | 0.500 | 0.500 | 0.500 | 0.500 |
| Coltsfoot HS | 0.500 | 0.500 | 0.500 | 0.500 | 0.500 | 0.500 |
| Sage HS | 0.500 | 0.500 | 0.500 | 0.500 | 0.500 | 0.500 |
| Bitter orange HS | 0.500 | 0.500 | 0.500 | 0.500 | 0.500 | 0.500 |
| Yarrow HS | 0.500 | 0.500 | 0.500 | 0.500 | 0.500 | 0.500 |
| Pemulen TR-2 ® | 1.350 | 1.300 | 0.500 | 0.500 | 0.500 | 0.500 |
| Phospholipid PTC ® | — | — | 1.300 | 1.300 | 1.300 | 1.300 |
| Phase C | | | | | | |
| Cremophore RH40 ® | 1.600 | 1.600 | 1.600 | 1.600 | 1.600 | 1.600 |
| Procetyl-10 ® | 0.800 | 0.800 | 0.800 | 0.800 | 0.800 | 0.800 |
| α-Bisabolol, natural | 0.500 | 0.500 | 0.500 | 0.500 | 0.500 | 0.500 |
| Vitamin E acetate | 0.200 | 0.200 | 0.200 | 0.200 | 0.400 | 0.400 |
| Vitamin E | — | — | — | — | — | 0.100 |

-continued

| | | | | | |
|---|---|---|---|---|---|
| linoleate | | | | | |
| Vitamin A palmitate | 0.050 | 0.050 | | | |
| Tea tree oil | 0.050 | 0.050 | 0.050 | 0.050 | 0.080 | 0.080 |
| % Reduction in average blemish size overnight | −7 | −18 | −17 | −3 | −28 | −34 |

*HS indicates a 2% by weight dry extract in propylene glycol.

The clinical studies were conducted with from 7 to 13 panelists. Average percentage size change of blemishes were determined after overnight treatment. The results, as listed in the table above, demonstrate the effectiveness of including dipotassium glycyrrhizinate (DPG) into the mask product. Formula 21 containing 0.1% dipotassium glycyrrhizinate exhibited an 18% reduction in average blemish size compared to the 7% of Formula 20, wherein DPG was absent. The effectiveness of salicylic acid was also demonstrated by comparison of Formula 22 (1.3% salicylic acid) exhibiting a 17% blemish size reduction by contrast with Formula 23 (0.5% salicylic acid) with only a 3% blemish size reduction.

The foregoing description and examples illustrate selected embodiments of the present invention. In light thereof, various modifications will be suggested to one skilled in the art, all of which are within the spirit and purview of this invention.

What is claimed is:

1. A cosmetic composition in an effective amount for treatment of pimples, blemishes and redness comprising:
   (i) from about 0.1 to about 10% of at least one keratolytic agent each selected from the group consisting of salicylic acid and salts thereof, $C_1$–$C_{25}$ α-hydroxy carboxylic acids and salts thereof, and mixtures thereof,
   (ii) from about 0.0001 to about 5% by weight each of an anti-irritancy agent combination which includes:
      (a) a water-soluble anti-irritancy material which is a $C_{20}$–$C_{100}$ saponin ;and
      (b) a water-insoluble anti-irritancy agent selected from the group consisting of $C_7$–$C_{30}$ polycyclic polyenes, $C_{15}$–$C_{40}$ triterpenes and mixtures thereof, the water-soluble and water-insoluble anti-irritancy agents being present in a relative weight ratio from about 20:1 to 1:20; and
   from about 1 to about 99.9% by weight of a cosmetically acceptable carrier.

2. A composition according to claim 1 wherein the at least one keratolytic agent comprises from about 0.1 to about 10% by weight of salicylic acid and also from about 0.1 to about 10% by weight of a $C_1$–$C_{25}$ α-hydroxy carboxylic acid.

3. A composition according to claim 2 wherein the $C_1$–$C_{25}$ α-hydroxy carboxylic acid is selected from the group consisting of glycolic acid, lactic acid, 2-hydroxy octanoic acid and combinations thereof.

4. A composition according to claim 2 wherein the composition further comprises from about 0.01 to about 5% by weight of $C_1$–$C_{10}$ alkyl lactate.

5. A composition according to claim 1 wherein the water-soluble anti-irritancy agent is diglycyrrhizinic acid and salts thereof.

6. A composition according to claim 5 wherein the water-soluble anti-irritancy agent is selected from the group consisting of dipotassium glycyrrihizinate and ammonium glycyrrihizinate.

7. A composition according to claim 1 wherein the water-insoluble anti-irritancy agent is selected from the group consisting of α-bisabolol, azulene and combinations thereof.

8. A composition according to claim 1 further comprising from about 0.1 to about 5% by weight of aloe extract.

9. A method for reducing the size of facial blemishes comprising applying to the face an effective amount of a cosmetic composition comprising:
   (i) from about 0.1 to about 10% of at least one keratolytic agent each selected from the group consisting of salicylic acid and salts thereof, $C_1$–$C_{25}$ α-hydroxy carboxylic acids and salts thereof, and mixtures thereof,
   (ii) from about 0.0001 to about 5% by weight each of an anti-irritancy agent combination which includes:
      (a) a water-soluble anti-irritancy material which is a $C_{20}$–$C_{100}$ saponin ;and
      (b) a water-insoluble anti-irritancy agent selected from the group consisting of $C_7$–$C_{30}$ polycyclic polymers, $C_{15}$–$C_{40}$ triterpenes and mixtures thereof, the water-soluble and water-insoluble anti-irritancy agents being present in a relative weight ratio from about 20:1 to 1:20; and
   (iii) from about 1 to about 99.9% by weight of a cosmetically acceptable carrier.

\* \* \* \* \*